United States Patent [19]

Theeuwes

[11] 4,217,898
[45] Aug. 19, 1980

[54] SYSTEM WITH MICROPOROUS RESERVOIR HAVING SURFACE FOR DIFFUSIONAL DELIVERY OF AGENT

[75] Inventor: Felix Theeuwes, Los Altos, Calif.

[73] Assignee: Alza Corporation, Palo Alto, Calif.

[21] Appl. No.: 953,907

[22] Filed: Oct. 23, 1978

[51] Int. Cl.³ .............................................. A61M 31/00
[52] U.S. Cl. ............................................................. 128/260
[58] Field of Search .................. 128/127, 130, 213 R, 128/222, 260–261, 270–271; 424/19, 22, 16

[56] References Cited

U.S. PATENT DOCUMENTS

| | | | |
|---|---|---|---|
| 2,478,182 | 8/1949 | Consolazio . | |
| 2,846,057 | 8/1958 | Polin . | |
| 2,928,770 | 3/1960 | Bardani . | |
| 2,987,445 | 6/1961 | Levesque . | |
| 3,146,169 | 5/1965 | Stephenson . | |
| 3,538,214 | 11/1970 | Polli et al. | 424/19 |
| 3,938,515 | 2/1976 | Leeper et al. | 128/260 |
| 3,948,254 | 4/1976 | Zaffaroni | 128/130 |
| 3,977,404 | 8/1976 | Theeuwes | 128/260 |

OTHER PUBLICATIONS

*Acta Pharm. Suecia,* vol. 8, pp. 153–168, 1971, Sjorgen.
*J. Pharm. Sci.,* vol. 60, pp. 1028–1033, 1971, Arcy et al.

Primary Examiner—C. Fred Rosenbaum
Attorney, Agent, or Firm—Paul L. Sabatine; Edward L. Mandell; Thomas E. Ciotti

[57] ABSTRACT

A system is disclosed for delivering an active agent to a fluid environment of use. The system comprises a microporous reservoir, an active agent housed in the reservoir, a surface that defines an exposed area of the reservoir for releasing agent from the reservoir to the environment, and a wall impermeable to both fluid and agent that surrounds the remaining, unexposed surfaces of the reservoir. In operation, when the system is in the environment with the exposed surface presented to fluid, fluid enters the system through the exposed surface causing agent to diffuse from within the system, which agent is released from the exposed surface of the system to the environment at a controlled rate over time.

16 Claims, 8 Drawing Figures

SYSTEM WITH MICROPOROUS RESERVOIR HAVING SURFACE FOR DIFFUSIONAL DELIVERY OF AGENT

FIELD OF THE INVENTION

This invention pertains to a diffusional system for delivering a useful agent at a controlled rate over a prolonged period of time to a fluid environment of use.

BACKGROUND OF THE INVENTION

Devices made from porous materials for the controlled and continuous delivery of an active agent are known to the prior art. Generally, the agent is embedded in the material and its release therefrom often is adversely influenced by internal and external conditions. For example, U.S. Pat. No. 2,478,182 issued to Consolazio discloses a tablet comprising compressed granules of a common salt that pass through a No. 40 U.S. standard sieve, about 420 micron size. The tablet has an internally disposed cellular stroma of a thin, permeable dialyzing film. The film is made of cellulose acetate or cellulose nitrate. The cells of the stroma contain the salt so that, in dissolution, fluid dialyzes into the cellular compartment and the material dialyze out. The Consolazio patent also discloses that when the cellular compartments become engorged with fluid, the compartment burst and the desired substance is liberated therefrom to the exterior of the tablet. This mechanism for the salt results in a solution time of about 60 to 80 minutes for a ten grain tablet. The salt is released in this short time because the tablets of Consolazio are basically all salt with a little polymer binder. The tablet of Consolazio example contains 0.65 grain of salt and about 4 mg of polymer, and it has a salt to polymer ratio of 9 to 1, and for a 10 grain salt tablet, a salt to polymer ratio of about 16 to 1. The large size of Consolazio's salt granules coupled with these kinds of ratios lead to release by bulk-flow and quick spill-out to the surrounding fluid. These features preclude the use of the tablets as controlled, prolonged, diffusional agent delivery devices.

The prior art also includes U.S. Pat. No. 2,846,057 issued to patentee Polin. This patent discloses a device consisting of a porous cellophane wall surrounding sodium fluoride, that is released by water flowing into the pores to dissolve and leach it from the device. Controlled release is hard to obtain with this device because release is governed by external conditions and not by the device. That is, the amount of fluoride released changes with the rate of flow of water, with higher rates increasing the amount released, and lower rates decreasing the amount released over time. The patent does not teach a multi-structured system having a given surface area for controlled release over time. Another device is disclosed in United States Pat. No. 2,928,770 issued to Bardani. The device of the Bardani patent consists in a plurality of medicament layers separated by membranes having pores containing a pore closure substance. The pore closure substance is represented by a softened wax that is disclosed as being removable in the gastrointestinal tract by intestinal fluid. This device cannot be relied upon for controlled release as it requires in situ removal of the pore closure substance which is both difficult to achieve and is dominated by unregulated external conditions and not by the device per se.

In prior art U.S. Pat. No. 3,146,169 issued to Stephenson and Spence, there is disclosed a tablet formulation comprising a solid, inner medicated portion dissolvable in the fluid of the gastrointestinal tract. The portion is surrounded by an outer non-medicated portion which impermeable to medicament and fluids, insoluble, indigestible and unabsorbable in the fluid of the gastrointestinal tract. It appears the medicated portion is released by convection and diffusion. Delivery by convection will occur due to turbulence set up in the environment at the aperture of the tablet. This turbulence can exhibit a change in velocity that varies erratically in magnitude and direction, and as such the tablet does not lend itself for classification as a controlled, prolonged drug delivery device.

Similarly, in U.S. Pat. No. 3,538,214, Polli, Shoop and Grim disclose a device consisting of drug coated with a film of waterinsoluble plastic containing a modifying agent that is soluble at a certain pH. When this device is in the gastrointestinal tract, the modifying agent is partially or fully dissolved from the film by gastrointestinal fluid to form a porous film. This lets fluid through the film to dissolve the drug and leach it outwards through the pores into the tract. Controlled release is difficult to achieve with this device, because the selection of the modifying agent is based on the unknown acid and alkaline states of the gastrointestinal tract, which concomitantly influences pore formation and the exposure of drug to fluid. In U.S. Pat. No. 3,977,404, patentee Theeuwes discloses an osmotic device having a semipermeable wall and a microporous reservoir containing an agent that exhibits an osmotic pressure gradient across the semipermeable wall against an external fluid. The device releases agent by imbibing fluid through the semipermeable wall into the device, generating a hydrostatic pressure in the device that pumps agent from the device. The device operates by osmotic principles, and it cannot be converted to a diffusional device.

Another device designed for the release of drug from an inert plastic matrix is described by Sjorgen in *Acta Pharm. Suecia*, Volume 8, pages 153 to 158, 1971, and by D. Arcy, et at., in *J. Pharm. Sci., Volume* 60, pages 1028 to 1033, 1971. The device disclosed in these references consists of a porous poly(vinyl chloride) matrix having drug contained therein. Several disadvantages are associated with this device that tend to diminish its use as a reliable and dependable device. For example, the rate of release declines over time because the device lacks a means for governing the diffusional surface area exposed to a fluid environment of use. The unrestricted surface subjects the entire device to slight changes in the direction and velocity of fluid, which alters the amount and the rate of drug released by the device. Another disadvantage is the diffusional paths are not controlled in any direction, and as they increase and interact in all directions, the rate of release becomes unpredictable. Both of the above events cause the rate of release from the matrix to decrease as a function of time. These uncertainties restrict the application of the device, and present the rate of release from being known during its use. A similar device is set forth by Levesque in U.S. Pat. No. 2,987,445.

OBJECTS OF THE INVENTION

Accordingly, it is an immediate object of this invention to provide a novel system manufactured in the form of a device for delivering an active agent to produce a beneficial effect, which system overcomes the disadvantages associated with the prior art.

Still another object of the invention is to provide a delivery system that has a constant diffusional surface area which overcomes the declining delivery patterns associated with delivery systems having variable diffusional surface areas.

Yet another object of the invention is to provide drug delivery systems having a delivery pattern approaching a zero order profile, which systems represent an improvement over the delivery pattern of systems having first order release characteristics.

Still another object of the invention is to provide a delivery system that releases agent by diffusion, functions as a sustained release system over a prolonged period of time, and comprises a continuously forming microporous member having a diffusional surface area, with the remaining surface area of the microporous member carrying on its surface a coating of a material impermeable to both agent and aqueous-type fluids.

Still yet another object of this invention is to provide a diffusional device for delivering a drug over a range of release rates from very low to very high, which rates are controlled by the device and its components operating as an integral unit.

Yet another object of this invention is to provide an article of manufacture useful for making a drug delivery system, which article consists essentially of a microporous forming polymer housing drug and which polymer has part of its surface covered with a polymer impermeable to fluid and drug.

Other objects, features and advantages of this invention will be more apparent to those skilled in the art from the following detailed description taken in conjunction with the drawings and the accompanying claims.

SUMMARY OF THE INVENTION

This invention concerns a delivery system that releases agent by diffusion. The system consists essentially of a microporous reservoir having an exposed surface and an unexposed surface. The exposed surface is integral with the reservoir for releasing agent housed therein. The unexposed surface consists of a wall on the exterior surface of the reservoir, and it surrounds the reservoir except for the exposed surface. The wall is impermeable to both fluid and agent. The system releases agent by fluid entering the system through the exposed surface forming an agent formulation in the reservoir that is released by diffusion from the same exposed surface to a fluid environment of use. The invention also concerns an article of manufacture consisting essentially of a polymer impermeable to both fluid and agent in laminar arrangement with a polymer that forms a microporous structure in a fluid environment of use.

BRIEF DESCRIPTION OF THE DRAWINGS

In the drawings, which are not drawn to scale, but are set forth to illustrate various embodiments of the invention, the figures are as follows.

In the drawings and the specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1A:
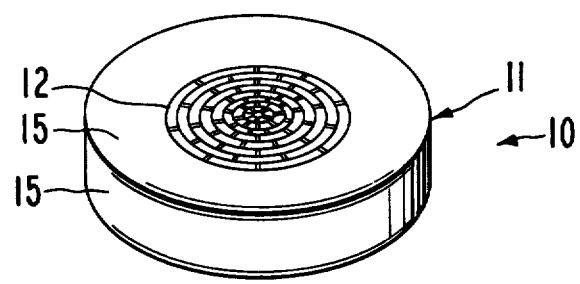
FIG. 1a is a view of a diffusional system of the invention designed to oral delivery of a beneficial drug.
Figure 1B:
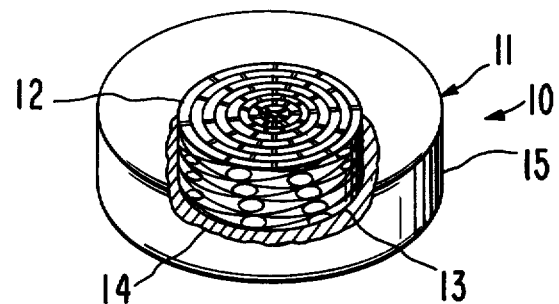
FIG. 1b is an open-sectioned view of the system of FIG. 1a depicting the internal structure of the system.

Turning now to the drawings in detail, which are examples of systems of this invention manufactured as delivery devices, and which examples are not to be construed as limiting, one embodiment of a system is indicated in FIGS. 1a and 1b by the numeral 10. System 10 comprises a body 11 having an exposed surface area 12 that is an integral surface of internal microporous reservoir 13. Reservoir 13 is seen in FIG. 1b at opened section 14 formed by removing a section of wall 15. Exposed surface area 12 communicates with internal reservoir 13 and the exterior of system 10. Microporous reservoir 13, as used for the purpose of this invention, embraces two embodiments. In one embodiment, reservoir 13 consists of a microporous forming polymer housing drug that is released by diffusion in a fluid environment to form a microporous reservoir having interconnected paths and micropores. In another embodiment, reservoir 13 is a preformed microporous polymer having interconnected channels and paths filled with drug that is released during use. A wall, 15, surrounds the unexposed surface of reservoir 13. Wall 15 is impermeable to the passage of aqueous and biological fluids and it is also impermeable to the passage agents including drugs.

In operation, an agent or drug is released from system 10 by external fluid diffusing into reservoir 13 through exposed surface 12 to form an agent formulation of solution and dissolved agent. The formulation is released from system 10 by its diffusing through the preformed or presently forming microporous paths and interconnected channels from exposed surface 12 to the exterior of system 10. The amount of agent released from system 10 having a planar surface 12 and an essentially homogeneous reservoir 13 is given by the expression dm/dt equals S×Q, wherein dm/dt is the release rate or mass per unit time, S is the surface area of the releasing surface, and Q is given by the espression:

$$Q = \sqrt{(D\epsilon/\tau)(2a - \epsilon C_s)C_s t}$$

wherein Q is the amount of agent released after time t per unit exposed surface area, D is the diffusivity of agent in the diffusing permeating external fluid, $\tau$ is the tortuosity factor of the microchannelled system, A is the total amount of agent present in the reservoir per unit volume, $C_s$ is the solubility of agent in the permeating fluid, and $\epsilon$ is the porosity of the reservoir.

Figure 2:
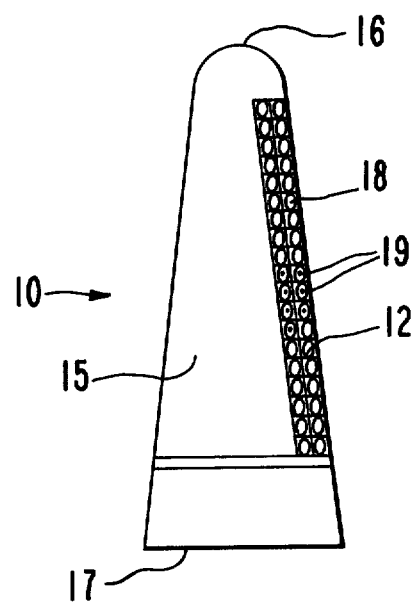
FIG. 2 is a view of another embodiment of the invention showing a side view of a diffusional device having an exposed planar surface with the system made as a device for delivering drug in the vaginal and anal canals.

FIG. 2 illustrates another system 10 manufactured, designed, sized, shaped and adapted as a device for administering drug within a body opening, the anal and vaginal canals, not shown. Device 10 is shaped like an obelisk having a lead end 16, a rear end, an exposed substantially planar surface 12, and an impermeable wall 15 that surrounds in part an internal microporous reservoir as seen in FIG. 1b. Reservoir 13 is preformed, or formed in the environment of use, of a polymeric material having a sponge-like appearance with numerous interconnected micropores 18. Agent 19, seen as dots in the micropores of surface 12, is dispersed throughout reservoir 13 and it is released by the diffusional mechanisms described above.

Figure 3:
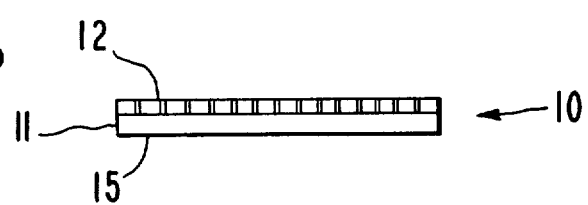
FIG. 3 shows a diffusional system fabricated as an implant with a planar surface for releasing an implant-releasable drug.

FIG. 3 depicts a system 10 manufactured as an implant device for releasing an implant releasable drug to a biological environment over time.

Figure 4:
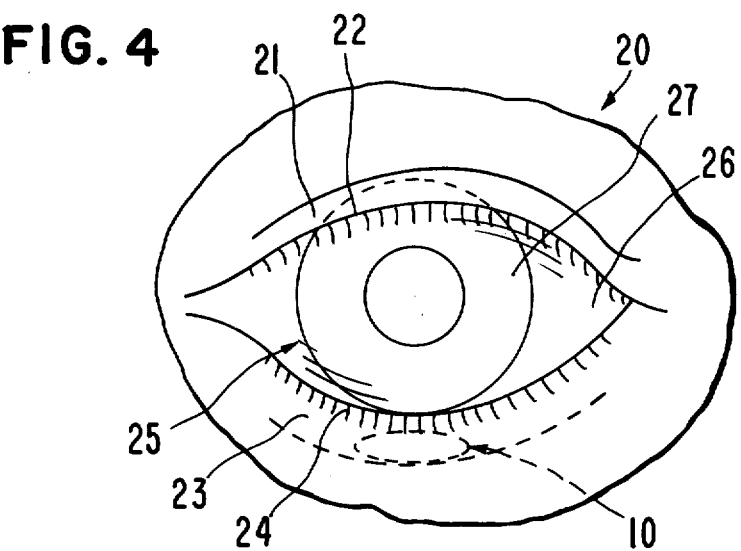
FIG. 4 is a partly diagrammatic front elevational view of a human eye illustrating an ocular device in ophthalmic drug delivery operative position after insertion in the eye.

FIG. 4 illustrates another embodiment of the invention, an ocular device for delivering drug to any eye 20. Device 10 is formed of a nonallergenic, biologically inert, insoluble in tear fluid materials, and it embodies the structure described above. Device 10 administers drug to eye 20 at a metered dosage rate. Eye 20 is comprised of an upper eyelid 21 with eyelashes 22 and a lower eyelid 23 with eyelashes 24. Eye 20 is anatomically comprised of eyeball 25 covered for the greater part by sclera 26 and its central area by cornea 27. Eyelids 21 and 23 are lined with an epithelial membrane or palpebral conjunctiva, and sclera 26 is lined with a bulbar conjunctiva that covers the exposed surface of eyeball 25. Cornea 27 is covered with a transparent epithelial membrane. The portion of the palpebral conunctiva which lines the upper eyelid and the underlying portion of the bulbar conjunctiva defines an upper cul-de-sac, while that portion of the palpebral conjunctiva which lines the lower eyelid and the underlying portion of the bulbar conjunctiva defines a lower cul-de-sac. Ocular diffusional device 10 is seen in broken continuous lines in the lower sac, and it is held in place by the natural pressure of the lower eyelid.

Figure 5A:
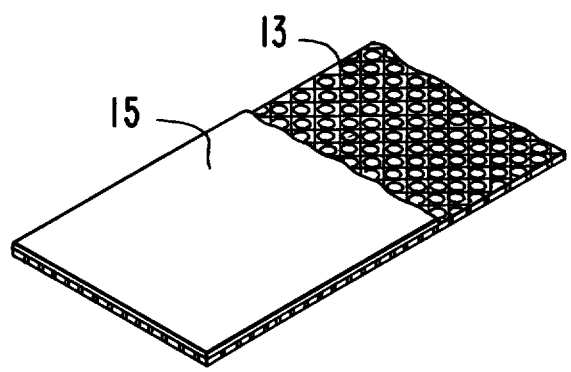
FIGS. 5a and 5b illustrate manufactures provided by the invention that are useful for fabricating diffusional systems; and, FIG. 6 is a graft depicting the release pattern obtained by using the systems of this invention.
Figure 5B:
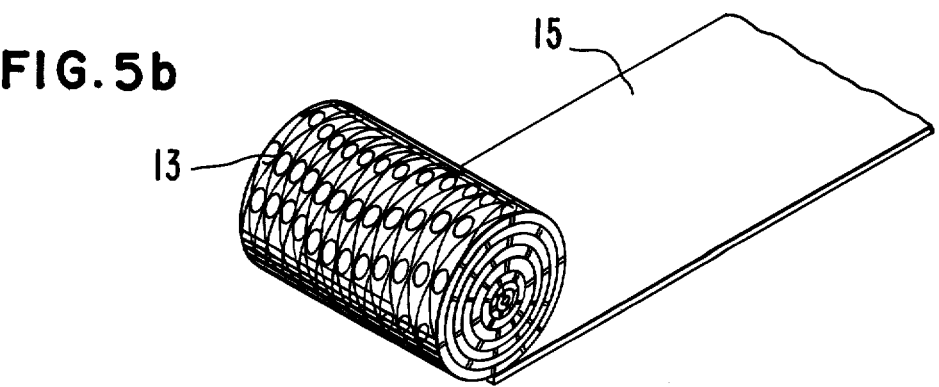

FIGS. 5a and 5b depict two articles of manufacture provided by the invention. FIG. 5a illustrates a microporous forming polymer 13 in laminar arrangement with an impermeable polymer having a rolllike shape unwound from an impermeable wall 15 that prevents its exposure to the environment. The articles are used for manufacturing delivery devices.

While FIGS. 1 through 4 are illustrative of various devices that can be made according to this invention, it is understood these devices are not to be construed as limiting, as the devices can have a wide variety of shapes, sizes, and forms adapted for delivering beneficial agents to different environments of use. For example, the devices include buccal, pessaries, prosthetic, artificial gland, cervical, intrauterine, ear and nasal devices. The devices include ocular devices of any geometric shape for comfortable retention in the eye. These shapes include ellipsoid, bean, banana, circular, rectangular, doughnut, crescent, and half-circle devices. In cross-section, the devices can be doubly convex, concavo-convex, rectangular and the like, and in use, the device will tend to conform to the shape of the eye. The dimensions of the ocular device can vary widely with the lower limit governed by the amount of drug to be supplied to the eye as well as the smallest sized device that can be placed in the eye. The upper limit on the size of the device is governed by the space limitation in the eye consistent with comfortable retention in the eye. Satisfactory eye devices generally have a length of 4 to 20 millimeters, a width of 1 to 15 millimeters and a thickness of 0.1 to 4 millimeters. The ocular device can house from 0.5 micrograms to 150 milligrams of drug, or more, and it can be made from materials that maintain their physical and chemical integrity.

The devices made for oral use can have various shapes and sizes, such as round with a diameter of 3/16 inch to ½ inch, or it can be shaped like a capsule having a range of sizes from triple zero to zero, and from 1 to 8. The devices also can be adapted for delivering an active agent in streams, aquariums, fields, factories, reservoirs, laboratory facilities, hot houses, transportation means, hospitals, veterinary clinics, nursing homes, and other environments of use.

DETAILED DESCRIPTION OF THE INVENTION

In accordance with the practice of this invention, it has now been found the devices provide many advantages over previously diffusional devices. One advantage is the ease of construction of the devices by standard manufacturing techniques. Another advantage of the invention is the device can be made with minimum number of parts. Another advantage for the device is the rate of release for a given surface can be controlled and the direction of release can be preselected by orientating the releasing surface to a preselected direction. Other advantages will become more apparent to those versed in the art from the specification, the drawings and the accompanying claims.

The phrase microporous reservoir is used for the present purpose denotes a microporous reservoir that is formed in situ from a material capable of forming said reservoir and housing an agent, which reservoir is formed during the release of agent, and it also denotes a microporous reservoir that is preformed and precharged with agent. In both embodiments, the microporous materials suitable for making the device can be described as forming or having a sponge-like appearance that provides a supporting structure for microscopic sized interconnected micropores or microvoids. The material can be isotropic, wherein the structure is homogeneous throughout a cross-sectional area, or they can be anisotropic, wherein the structure is non-homogeneous throughout a cross-sectional area. The micropores can be continuous, as they interconnect through tortuous paths of regular and irregular shapes in the reservoir. The shapes can be curved, curved-linear, randomly oriented mixed paths, hindered connected pores, straight connected and branched pores, and other micropores discernible by microscopic examination. Generally, the final microporous materials are defined by the pore size, the number of pores, the tortuosity of the microporous path, and the porosity which relates to the size and the number of pores. The pore size of a microporous material can be ascertained by measuring the observed pore diameter under the electron microscope. Generally, materials forming or possessing from 5 to 95% pores and having a pore size from 30 angstroms to 100 microns can be used for the reservoir. The pore size, number of pores, pore radius, length of path and other characteristics can be measured by procedures recorded in *Science*, Volume 170, pages 1302 to 1305, 1970; *Nature*, Volume 214, page 285, 1967; *Polymer Engineering and Science*, Volume 11, pages 284 to 288, 1971; *Industrial Processing With Membranes*, by Lacey and Loeb, pages 131 to 134, 1972, published by Wiley, Interscience, New York; in *Transport Phenomena in Membranes*, by Lakshminatayanaiah, Chapter 6, 1969, published by Academic Press, Inc., New York; in U.S. Pat. Nos. 3,567,809; 3,751,536, and 3,929,509.

Microporous materials are commercially available and they can be made by art-known methods. The materials having preformed microporous properties can be made by etched nuclear tracking, by cooling a solution of flowable polymer below the freezing point, whereby solvent evaporates from the solution in the form of crystals dispersed in the polymer and then curing the polymer followed by removing the solvent crystals by cold or hot stretching at low or high temperatures until pores are formed, by leaching from a polymer a soluble component by an appropriate solvent, by ion exchange reaction and by polyelectrolyte processes. Processes for preparing microporous materials are described in *Synthetic Polymer Membranes*, by Kesting, Chapters 4 and 5, 1971, published by McGraw Hill, Inc.; *Chemical Reviews, Ultrafiltration*, Volume 18, pages 373 to 455, 1934; *Polymer Engineering and Science*, Volume 11, No. 4, pages 284 to 288, 1971; *J. Appl. Poly. Sci.*, Volume 15, pages 811 to 829, 1971; and in U.S. Pat. Nos. 3,376,238; 3,565,259; 3,615,024; 3,751,536; 3,801,682; 3,849,528; and 3,852,224. The micropores of a preformed material can be charged with agent by soaking the microporous material in a solution having a known concentration of agent which includes saturated and supersaturated. Next, the liquid of the solution is controllably evaporated, leaving the microporous reservoir charged with agent. Manufacturing procedures are described in *Modern Plastic Encyclopedia*, Volume 46, pages 62 to 69, 1969; in Remington's *Pharmaceutical Science*, 14th Edition, pages 1649 to 1968, 1970, published by Mack Publishing Company, Easton, Penn.; and in *The Theory and Practice of Industrial Pharmacy*, by Lackman, et al, pages 197 to 225, 1970, published by Lea Febiger, Philadelphia, Penn.

The reservoir of a device leading to a microporous reservoir that is formed in situ during release of agent is manufactured by standard techniques. For example, one suitable method for making a microporous reservoir consists essentially of blending a polymeric powder with an agent in crystalline or granular form, and then applying pressure with heat to convert the blend into a solid having agent releasably charged therein. The solid is shaped, sized and adapted into the desired reservoir size. In operation, agent will be released by diffusion forming a microporous reservoir with interconnecting voids, pores and channels. Another method for making the reservoir consists in dispersing an agent in a liquid monomer and then polymerizing the monomer to yield a dispersion of agent in polymer. The reservoir is sized and shaped to the dimensions of the device.

Materials useful for making microporous reservoir for both of the structural embodiments described herein include polycarbonates, polymers prepared by the phosgenation of dihydroxyl aromatics such as bisphenol A, poly(vinylchloride), polyhexamethylene adipamide, polyolefins, relatively crystalline polymers such as polyalkylene sulfide, polycaprolactam and polyethylene terephthalate, polychlororethers, polyesters prepared by esterification of a dicarboxylic acid or anhydride with an alkylene polyol, hydrophobic or hydrophilic microporous homopolymers, copolymers or interpolymers having a reduced bulk density and materials as described in U.S. Pat. Nos. 3,595,752; 3,643,178; 3,654,066; 3,709,774; 3,718,532; 3,806,061; 3,852,224; 3,852,388; and 3,853,601; in British Pat. No. 1,126,849; and in *Chem. Abst.* Volume 71, 4274f, 22572f, 22573f, 1969.

The materials suitable for forming the wall that serves to prevent fluid from reaching, and agent from leaving the unexposed surface of the reservoir include materials substantially impermeable to the passage of fluid and agent. Representative materials include copolymers of vinyl chloride with vinyl acetate, styrene, acrylonitrile, dialkyl fumurate or vinylidene chloride, blends or polyvinyl chloride and chlorinated polyethylene, copolymers of vinylidene chloride, for example, with vinyl chloride, graft polymers of polypropylene with butylene, barrier polymers of 85% vinylidene chloride and 15% vinyl chloride, or 90% vinylidene chloride and 10% vinyl chloride, polyvinylidene halide formed of a vinylidene halide and a vinyl halide, polyvinylidene chloride coated with a fatty acid salt of 12 to 22 carbons including sodium and potassium salts of lauric, myristic, palmitic and the like, acrylonitrile-styrene copolymer, acrylonitrilebutadiene-styrene terpolymer, poly(monochlorotrifluoroethylene), poly (tetrafluoroethylene), tetrafluoroethylene-hexafluoroethylene copolymer and vinyl chloride-acrylonitrile copolymer.

The expression active agent as used herein broadly includes any beneficial compound composition of matter that can be delivered from the device to produce a beneficial and useful result. The agents include algicides, anti-oxidants; air-purifiers, biocides, herbicides, pesticides, germicides, rodenticides, fungicides, insecticides, plant growth promoters, plant growth inhibitors, preservatives, disinfectants, sterilization agents, foods, food supplements, nutrients, drugs, vitamins, sex sterilants, fertility inhibitors, fertility promoters, microorganism attenuators, and other agents that benefit the environment of use.

The term drug includes any physiologically or pharmacologically actice substance that produces a local or systemic effect in a biological environment. The phrase biological environment includes animals, avians, reptiles and pices. The term animal includes mammals, humans, primates, domestic household, sport and farm animals, laboratory, zoo and jungle animals. The active drug can be an inorganic or organic compound including drugs that act on the central nervous system, hypnotics, sedatives, psychic energizers, tranquilizers, monoamine oxidase inhibitors, anticonvulsants, muscle relaxants, antiparkinson drugs, analgesics, antiinflammatory, anesthetics, anti-spasmodic, muscle contractant, prostaglandin, anti-microbial, hormones, estrogens, progestins, progestational steroids, sympathomimetic, cardiovascular, diuretic, antiparasitic, neoplastic, hypoglycemic, opthalmic, electrolytes and the like. The beneficial drugs and their conventional doses are known in *Remington's Pharmaceutical Sciences*, 14th Edition, 1970, published by Mack Publishing Company, Easton, Pa.; and in the *The Pharmocological Basis of Therapeutics*, by Goodman and Gilman, 4th Edition, 1970, published by the MacMillian Company, London.

The amount of agent housed in the device is initially in excess of the amount that can be dissolved in the fluid that enters the microporous reservoir through the exposed surface. Under the physical state, when the amount of solid agent is in excess, the device will operate by diffusion to give a controlled, substantially constant rate of release. Also, the rate of agent release pattern can be varied by having different amounts of agent in the reservoir to form solutions containing different concentrations of agent for delivery from the device to an aqueous or biological fluid environment. Generally, the device can house from 0.02 ng to 7.5 g or more, with individual devices containing, for example, 1 mg, 5 mg, 100 mg, 250 mg, 500 mg, 1.5 g and the like.

The following examples are merely illustrative of the present invention and they should not be considered as limiting the scope of the invention in any way, as these examples and other quivalents thereof will become apparent to those versed in the art in the light of the present disclosure, the drawings and the accompanying claims.

EXAMPLE 1

A diffusional device for the controlled and continuous release of the replenishing electrolyte salt potassium chloride is manufactured as follows: first, a commercially available matrix consisting essentially of microporous poly(vinylchloride) is charged with 750 mg of potassium chloride. Then, the matrix is sized and shaped as a tablet designed and adapted for oral use. Next, one of the slightly curved surfaces and the circumferential surface of the tablet are coated with a fluid and electrolyte impermeable coating of copolymeric vinyl chloride and vinylidene chloride. The coating is applied from a 10% solution of tetrahydrofuran. Care is taken to avoid coating the uncoated, exposed distant slightly curved surface of the tablet, thereby keeping the releasing surface area constant. The coating has a thickness of 1.5 mils, and the tablets are dried at 50° C. for 48 hours to remove residual solvent.

The release rate for the device is measured in a bath consisting of a series of 15 test tubes with each tube containing 25 ml of distilled water at 37° C. The test is carried out by placing the device in the first tube for 1 hour, then the device is transferred to the second tube for one hour, and then in repeat fashion into the remaining tubes. The device is slowly oscillated throughout the test in the tubes. The amount of potassium chloride delivered is determined by electrical conductive measurements for each tube using a conductive meter that is calibrated with known standards.

Figure 6:
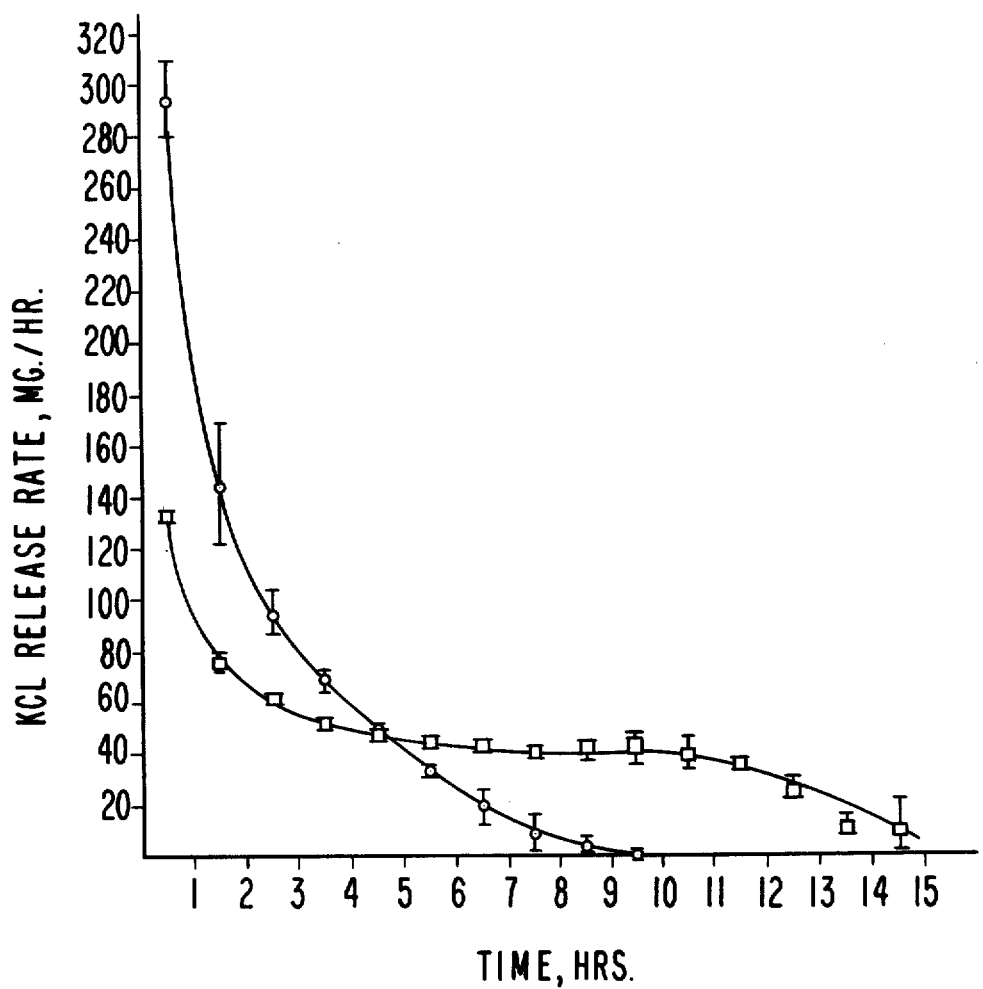

The results of the measurements are illustrated in FIG. 6. The steep, declining curved line connected through circles is the release rate for a 100% uncoated, poly(vinylchloride) reservoir containing 750 mg of potassium chloride. The substantially linear line connected through squares indicates the release rate for the microporous, poly(vinylchloride) tablet containing 750 mg of potassium chloride having the exposed and unexposed surfaces described immediately above. The recorded results each illustrate an average of three measurements. The straight lines drawn through the circles and squares indicates the range of experimental data.

EXAMPLE 2

A rectangular-shaped oral, sustained release drug delivery device is manufactured as follows: first, a microporous forming reservoir is made by dissolving the copolymer of vinyl acetate-vinyl chloride in a granulating medium consisting of 5% colophony in 70% ethanol. Then, granules of theophylline monoethanol amine are mixed therewith and the solvent removed to produce dry granules of copolymer and drug. Next, a mold 10 mm long, 5 mm wide and 5 mm deep is charged with the granules and compressed under high pressure to yield a stable, inert, reservoir consisting of drug embedded in a microporous forming reservoir. The copolymer is non-reactive with the drug and the microporous reservoir does not disintegrate, but remains intact in the gastrointestinal tract. Next, all the long sides of the rectangle are coated with impermeable copolymer styrene-butadiene in tetrahydrofuran. Finally, the latter is removed leaving the distant ends of the device exposed for release of drug by diffusion.

EXAMPLE 3

An oral, controlled release system having an exposed, planar surface, which system consists of quinidine gluconate particles incorporated in a microporous forming reservoir, with the quinidine gluconate released by the combined diffusion action of the system and the fluid in the environment that enters the system according to the equation: $Q = \{D\epsilon/\tau \cdot C_s t \cdot (2A - C_s)\}^{\frac{1}{2}}$, wherein Q is the amount quinidine gluconate released per unit area of surface at time t, D is the diffusion coefficient of quinidine gluconate in the fluid that enters the system, $\epsilon$ is the porosity of the formed, microporous reservoir, $C_s$ is the solubility of quinidine gluconate in the diffusing fluid, A is the concentration of drug in the reservoir, and $\tau$ is the tortuosity of the reservoir and is manufactured as follows: first, a quantity of high density polyethylene is added to a pulverizer equipped with a screen that classifies the produced particles to a preselected mesh size. Then, in a separate operation quinidine gluconate is added to the pulverizer and converted to particles. The polyethylene particles and the quinidine gluconate are blended in a cone blender to produce a well-mixed blend. Next, a series of molds shaped like an oral delivery device are filled with the blend and compressed under pressure. The pressed reservoirs then are removed from the mold, placed on a flat surface, and the visible areas coated with a 2 mil wall of poly(vinylidene chloride). In operation, quinidine gluconate is released through the exposed surface while the walled, unexposed areas are impermeable to the passage thereof.

While the invention has been illustrated and described in detail, it is not intended to be limited to the details disclosed, since various modifications and changes may be made without departing in any way from the spirit of the present invention.

I claim:

1. A diffusional device for the controlled dispensing of a beneficial agent to an environment of use, wherein the device comprises:
    (a) a reservoir formed of an inert material consisting of a multiplicity of micropores and micropaths, said reservoir having,
    (b) an exposed surface area for admitting an external fluid present in the environment of use and for dispensing an agent formulation formed in the reservoir to the environment,
    (c) a wall impermeable to both fluid and agent on the remaining surface area of the reservoir,
    (d) a beneficial agent housed in both the micropores and micropaths; and,
    (e) wherein, in operation when the device is in the environment of use, fluid in the environment enters the device through the exposed surface into the reservoir forming an agent formulation that is dispensed by diffusion from the exposed surface of device to the environment at a controlled rate over a prolonged period of time.

2. The diffusional device according to claim 1, wherein the amount of agent dispensed is:

$$Q = \sqrt{(D\epsilon/\tau)(2A - \epsilon C_s)C_s t}$$

wherein Q is the amount of agent dispensed after time t per unit exposed surface area, D is the diffusivity of the agent in the diffusing external fluid, $\tau$ is the tortuosity of the micropaths, A is the amount of agent present in the reservoir per unit volume, $C_s$ is the solubility of agent in the diffusing fluid, and $\epsilon$ is the porosity of the microporous reservoir.

3. The diffusional device for dispensing the beneficial agent according to claim 1, wherein the device is designed, shaped and adapted for dispensing drug, orally, in the vagina, and in the anal canal.

4. The diffusional device for dispensing the beneficial agent according to claim 1, wherein the wall is nonerodible and maintains its physical and chemical integrity in the presence of fluid in the environment.

5. The diffusional device for dispensing the beneficial agent according to claim 1, wherein the agent is a drug selected from the group consisting essentially of locally and systemically acting drugs.

6. The diffusional device for dispensing the beneficial agent according to claim 1, wherein the wall is formed of a polymeric material comprising vinylidene chloride that is impermeable to the passage of fluid and agent.

7. The diffusional device for dispensing the beneficial agent according to claim 1, wherein the environment of use is a human, the agent is a drug and the reservoir houses from 0.02 nanograms to 7.5 grams of said drug.

8. The diffusional device for dispensing the beneficial agent according to claim 1, wherein the reservoir consisting essentially of the micropores and micropaths is preformed and then charged with beneficial agent.

9. A diffusional device for the controlled dispensing of a beneficial agent to an environment of use, wherein the device comprises:
   (a) a reservoir comprising an inert material that forms micropores and microchannels in a fluid environment,
   (b) an exposed surface on the reservoir admitting an external fluid present in the environment into the reservoir and for dispensing an agent formulation formed in the reservoir to the environment,
   (c) a wall impermeable to both fluid and agent on the remaining surface of the reservoir,
   (d) a beneficial agent housed in the reservoir, and,
   (e) wherein, in operation when the device is in the environment of use, fluid in the environment enters the reservoir through the channels therein, with the formulation dispensed therethrough by diffusion from the exposed surface of the device to the environment at a controlled rate over a prolonged period of time.

10. The device for the controlled dispensing of beneficial agent according to claim 9, wherein the agent is a drug selected from the group consisting of locally and systemically acting drugs.

11. The diffusional device for the controlled dispensing of beneficial agent according to claim 9, wherein the environment of use is a human, the agent is a drug, and the device is sized, shaped and adapted for dispensing drug by oral, vaginal and anal administration over time.

12. The diffusional device for dispensing the beneficial agent at a controlled rate over time according to claim 9, wherein the amount of agent released from the reservoir is $Q = [D\epsilon/\tau \cdot C_s t \cdot (2A - \epsilon C_s)]^{\frac{1}{2}}$ wherein Q is the amount of agent released per unit area of exposed surface at time t, D is the diffusion coefficient of the agent in the fluid that enters the device, $\epsilon$ is the porosity of the formed microporous reservoir, $C_s$ is the solubility of the agent in the diffusing fluid, A is the concentration of agent in the reservoir, and $\tau$ is the tortuosity of the formed microchanneled reservoir.

13. The diffusional device for dispensing the beneficial agent according to claim 9, wherein the wall impermeable to fluid and agent is a polymeric material comprising vinylidene chloride.

14. The diffusional device for dispensing the beneficial agent according to claim 9, wherein the wall is inert, nonerodible, and keeps its physical and chemical integrity in the presence of fluid and agent.

15. The diffusional device for dispensing the beneficial agent according to claim 9, wherein the agent is soluble in fluid present in the environment, and the reservoir contains from 0.02 nanograms to 7.5 grams of agent.

16. A polymeric structure for manufacturing a device that dispenses a beneficial agent to a fluid environment of use over a prolonged period of time, comprising a film selected from the group consisting of vinyl chloride-vinyl acetate copolymer, vinyl chloride-styrene copolymer, vinyl chloride-acrylonitrile copolymer, vinyl chloride-vinylidene chloride copolymer, vinylidene chloride-acrylonitrile copolymer, polyvinylidene chloride, polyethylene, and styrene-butadiene copolymer in structured laminar arrangement with a polymeric microporous material consisting essentially of 5 to 95% interconnected pores of 30 angstroms to 100 micron size housing in the micropores a beneficial agent.

* * * * *